United States Patent
Onuma et al.

(10) Patent No.: US 9,662,134 B2
(45) Date of Patent: May 30, 2017

(54) ULTRASONIC PROBE, ULTRASONIC TREATMENT INSTRUMENT AND TREATMENT SYSTEM

(71) Applicant: OLYMPUS CORPORATION, Tokyo (JP)

(72) Inventors: Chie Onuma, Fuchu (JP); Manabu Ishikawa, Hachioji (JP); Sohei Ueda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/040,668

(22) Filed: Feb. 10, 2016

(65) Prior Publication Data

US 2016/0157884 A1 Jun. 9, 2016

Related U.S. Application Data

(63) Continuation of application No. PCT/JP2014/075459, filed on Sep. 25, 2014.
(Continued)

(51) Int. Cl.
*A61B 17/32* (2006.01)
*A61B 17/16* (2006.01)
(Continued)

(52) U.S. Cl.
CPC ...... *A61B 17/320068* (2013.01); *A61B 17/16* (2013.01); *A61B 17/1604* (2013.01);
(Continued)

(58) Field of Classification Search
CPC . A61B 17/3211; A61B 90/37; A61B 17/1628; A61B 17/320068; A61B 90/361;
(Continued)

(56) References Cited

U.S. PATENT DOCUMENTS

| 4,349,032 A * | 9/1982 | Koyata | A61B 1/00177 |
| | | | 600/139 |
| 5,540,693 A * | 7/1996 | Fisher | A61B 17/1659 |
| | | | 606/79 |

(Continued)

FOREIGN PATENT DOCUMENTS

| EP | 2 119 403 A1 | 11/2009 |
| JP | H05-168642 A | 7/1993 |

(Continued)

OTHER PUBLICATIONS

Apr. 7, 2016 International Preliminary Report on Patentability issued in International Application No. PCT/JP2014/075459.
(Continued)

*Primary Examiner* — Todd J Scherbel
*Assistant Examiner* — Son Dang
(74) *Attorney, Agent, or Firm* — Oliff PLC

(57) ABSTRACT

A contact portion, provided in an exposed surface of the treating section, treats a treated object by a transmitted ultrasonic vibration while intruding into the treated object toward an intruding direction from a state being in contact with the treated object. An index portion is disposed on an anti-intruding direction side with respect to the contact portion in the exposed surface. The index portion becomes an index indicating an intruding amount of the contact portion into the treated object toward the intruding direction. The index portion includes index surfaces arranged in the intruding direction, and each of the index surfaces has an angle relative to the intruding direction which is different from the angle of the adjacent index surface.

12 Claims, 10 Drawing Sheets

Related U.S. Application Data

(60) Provisional application No. 61/883,520, filed on Sep. 27, 2013.

(51) Int. Cl.
| | | |
|---|---|---|
| *A61C 1/07* | (2006.01) | |
| *A61B 17/3211* | (2006.01) | |
| *A61N 7/00* | (2006.01) | |
| *A61B 90/00* | (2016.01) | |
| *A61B 17/00* | (2006.01) | |
| *A61B 17/22* | (2006.01) | |

(52) U.S. Cl.
CPC ...... *A61B 17/1628* (2013.01); *A61B 17/3211* (2013.01); *A61B 90/361* (2016.02); *A61B 90/37* (2016.02); *A61C 1/07* (2013.01); *A61N 7/00* (2013.01); *A61B 2017/00398* (2013.01); *A61B 2017/22011* (2013.01); *A61B 2017/320072* (2013.01)

(58) Field of Classification Search
CPC .......... A61B 17/16; A61B 2017/00398; A61B 2017/320072; A61B 2017/22011; A61N 7/00

See application file for complete search history.

(56) References Cited

U.S. PATENT DOCUMENTS

| | | | | |
|---|---|---|---|---|
| 6,117,152 | A * | 9/2000 | Huitema | A61B 17/00008 601/2 |
| 6,497,715 | B2 * | 12/2002 | Satou | 604/22 |
| 2002/0103497 | A1 | 8/2002 | Satou | |
| 2004/0191725 | A1 * | 9/2004 | Szymaitis | A61C 3/02 433/165 |
| 2006/0253050 | A1 * | 11/2006 | Yoshimine | A61B 17/320068 601/2 |
| 2007/0060926 | A1 | 3/2007 | Escaf | |
| 2007/0065773 | A1 * | 3/2007 | Hickok | A61O 5/026 433/119 |
| 2008/0188878 | A1 * | 8/2008 | Young | A61B 17/14 606/169 |
| 2009/0318944 | A1 | 12/2009 | Kimura et al. | |
| 2010/0121197 | A1 | 5/2010 | Ota et al. | |
| 2010/0191173 | A1 | 7/2010 | Kimura et al. | |
| 2013/0204285 | A1 | 8/2013 | Gouery et al. | |
| 2014/0031726 | A1 * | 1/2014 | Chernomorsky | A61B 17/24 601/2 |
| 2014/0257272 | A1 * | 9/2014 | Clark, III | A61B 18/14 606/37 |
| 2015/0005795 | A1 * | 1/2015 | Darian | A61B 17/320068 606/169 |
| 2016/0175000 | A1 * | 6/2016 | Akagane | A61B 18/14 606/169 |

FOREIGN PATENT DOCUMENTS

| | | |
|---|---|---|
| JP | H07-255736 A | 10/1995 |
| JP | 2002-143177 A | 5/2002 |
| JP | 3120743 U | 4/2006 |
| JP | 2010-000336 A | 1/2010 |
| JP | 2013-099571 A | 5/2013 |
| JP | 2013-150675 A | 8/2013 |

OTHER PUBLICATIONS

Nov. 18, 2014 International Search Report issued in International Patent Application No. PCT/JP2014/075459.

Aug. 18, 2015 Office Action issued in Japanese Patent Application No. 2015-516307.

Apr. 13, 2017 Extended European Search Report issued in European Patent Application No. 14849531.0.

* cited by examiner

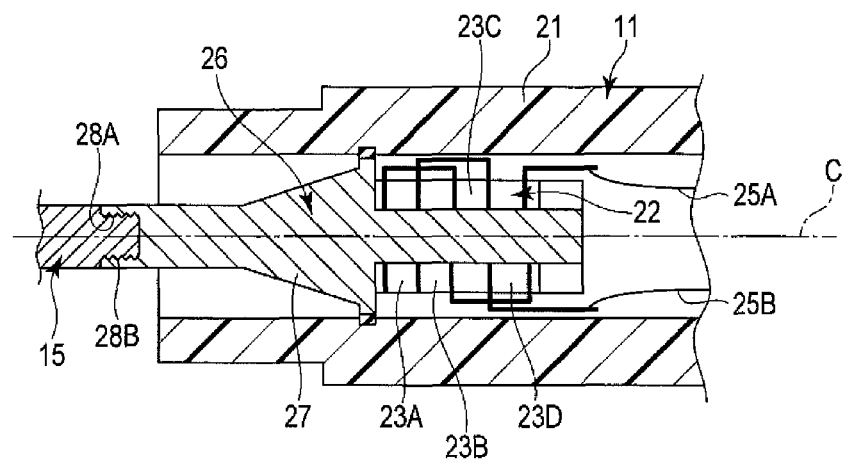
F I G. 2
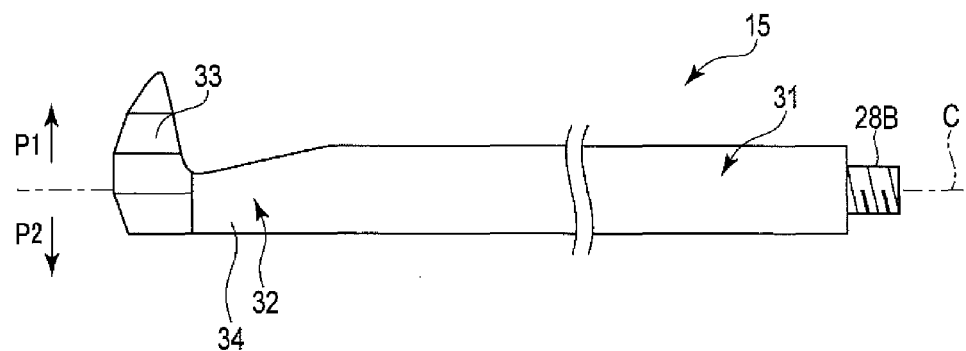
F I G. 3

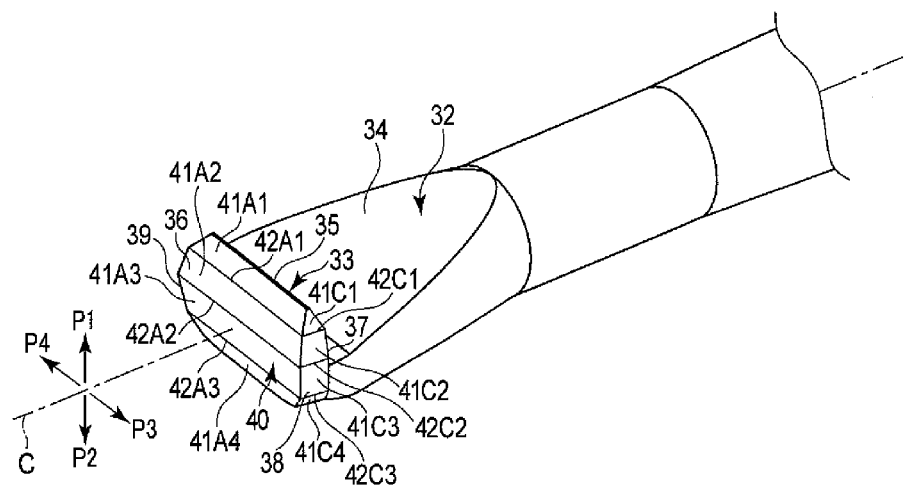
F I G. 4
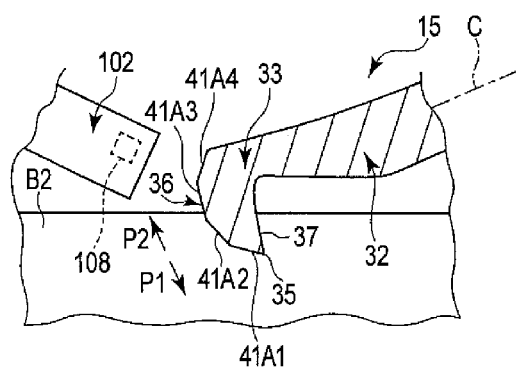
F I G. 5

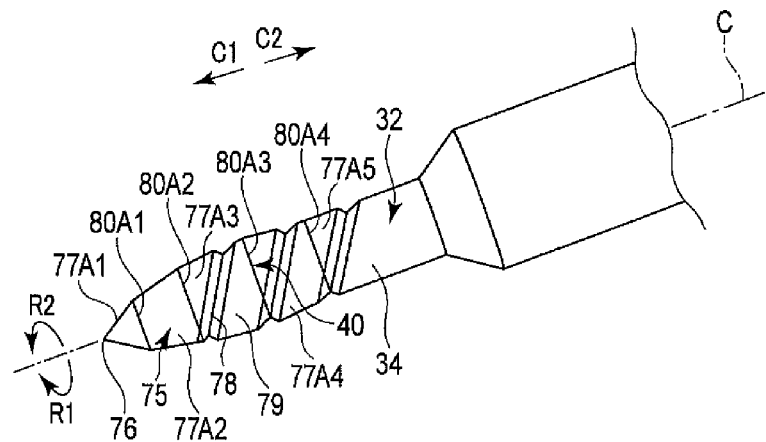
F I G. 14
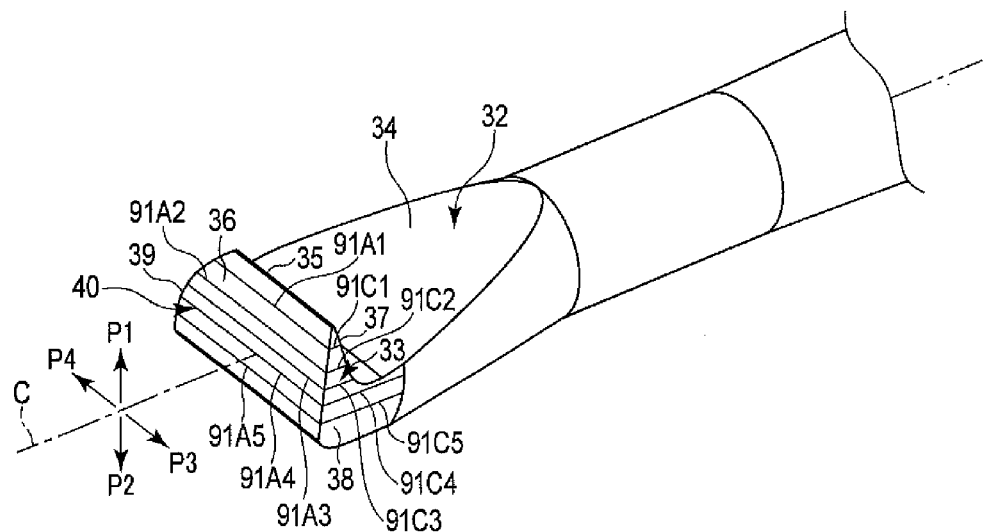
F I G. 15

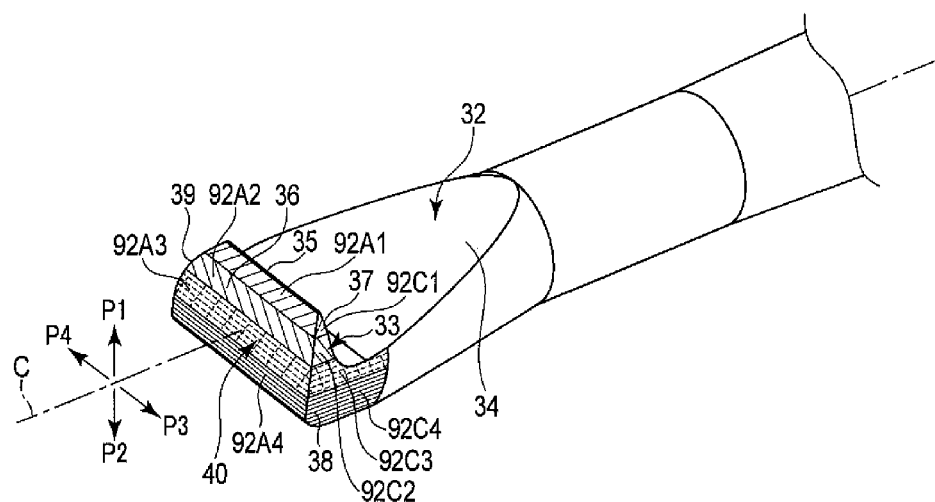
F I G. 16

ULTRASONIC PROBE, ULTRASONIC TREATMENT INSTRUMENT AND TREATMENT SYSTEM

CROSS-REFERENCE TO RELATED APPLICATIONS

This is a Continuation Application of PCT Application No. PCT/JP2014/075459, filed Sep. 25, 2014 and based upon and claiming the benefit of priority from prior U.S. Provisional Application No. 61/833,520, filed Sep. 27, 2013; and PCT Application No. PCT/JP2013/085122, filed Dec. 27, 2013, the entire contents of both of which are incorporated herein by reference.

BACKGROUND OF THE INVENTION

1. Field of the Invention

The present invention relates to an ultrasonic probe in which a treating section is provided in a distal portion, and the treating section treats a treated object by use of a transmitted ultrasonic vibration. Additionally, the present invention relates to an ultrasonic treatment instrument including the ultrasonic probe, and a treatment system including the ultrasonic treatment instrument.

2. Description of the Related Art

In Jpn. Pat. Appln. KOKAI Publication No. 2010-336, there is disclosed an ultrasonic treating instrument which resects a treatment object such as a bone by use of an ultrasonic vibration. This ultrasonic treating instrument includes an ultrasonic probe which is extended along a longitudinal axis and is configured to transmit the ultrasonic vibration from a proximal direction toward a distal direction. Further, in a distal portion of the ultrasonic probe, there is disposed a treating section configured to perform a treatment to resect the treated object by use of the transmitted ultrasonic vibration. In the treatment to cut the treated object, a contact portion provided in the treating section is brought into contact with the treated object. In this state, the treating section is vibrated by the ultrasonic vibration, thereby resecting the treatment object. By resecting the treated object, the contact portion intrudes into the treated object in an intruding direction. Additionally, a coating layer is formed on an exposed surface of the treating section. In the treatment to resect the treated object, on the basis of a range of the coating layer, an intruding amount of the contact portion into the treated object is recognized, and a resecting depth of the treated object is recognized.

BRIEF SUMMARY OF THE INVENTION

According to one aspect of the invention, an ultrasonic probe includes that: a probe main body extended along a longitudinal axis, and configured to transmit an ultrasonic vibration from a proximal direction toward a distal direction; and a treating section provided on a distal direction side with respect to the probe main body, and configured to perform a treatment of a treated object by use of the ultrasonic vibration transmitted via the probe main body, the treating section including: an exposed surface exposed to an outside; a contact portion provided in the exposed surface, and configured to treat the treated object by the transmitted ultrasonic vibration while intruding into the treated object toward an intruding direction from a state where the contact portion is in contact with the treated object; and an index portion which is disposed on an opposite direction side of the intruding direction with respect to the contact portion in the exposed surface, and which becomes an index indicating an intruding amount of the contact portion into the treated object toward the intruding direction, the index portion including index surfaces arranged in the intruding direction, each of the index surfaces having an angle relative to the intruding direction which is different from the angle of the adjacent index surface, wherein in the index portion, a ridgeline is formed between each of the index surfaces and the adjacent index surface, and the adjacent ridgelines are parallel to each other.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a cross-sectional view schematically showing a constitution of a transducer unit according to the first embodiment;

FIG. 3 is a schematic view showing a constitution of an ultrasonic probe according to the first embodiment;

FIG. 4 is a perspective view schematically showing a constitution of a treating section of the ultrasonic probe according to the first embodiment;

FIG. 5 is a schematic view showing a state where a treated object is resected with the treating section according to the first embodiment;

FIG. 14 is a perspective view schematically showing a constitution of a treating section of an ultrasonic probe according to a first modification of the third embodiment;

FIG. 15 is a perspective view schematically showing a constitution of a treating section of an ultrasonic probe according to a first reference example;

FIG. 16 is a perspective view schematically showing a constitution of a treating section of an ultrasonic probe according to a second reference example.

DETAILED DESCRIPTION OF THE INVENTION

First Embodiment

Figure 1:
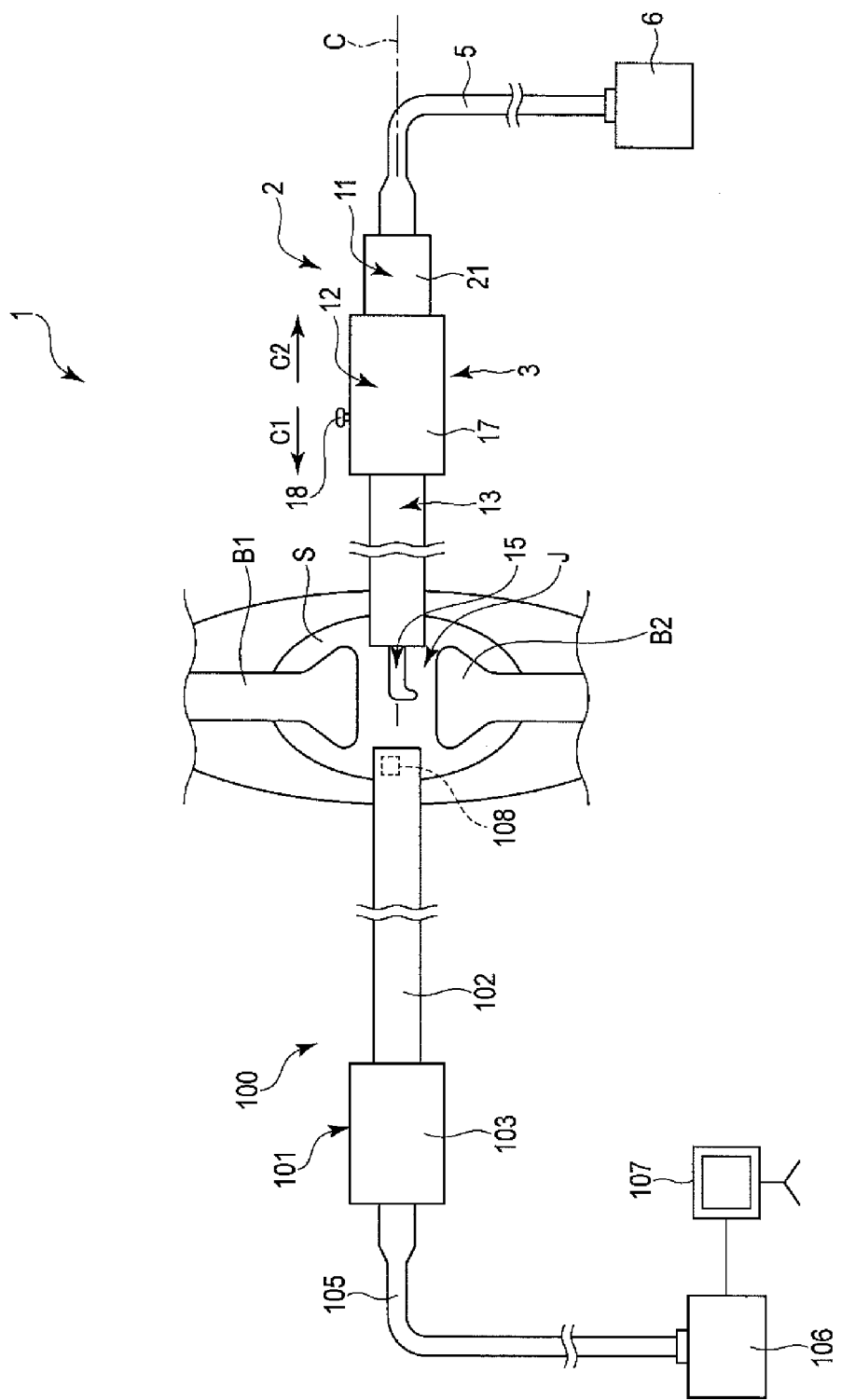
FIG. 1 is a schematic view showing a treatment system according to a first embodiment of the present invention.

A first embodiment of the present invention will be described with reference to FIG. 1 to FIG. 6. FIG. 1 is a view showing a treatment system 1 of the present embodiment. As shown in FIG. 1, the treatment system 1 is for use in, e.g., a treatment of a joint J between a bone B1 and a bone B2 in a shoulder, a knee or the like. The treatment system 1 includes an ultrasonic treatment apparatus 2, and an arthroscope apparatus 100 that is an endoscope device.

The arthroscope apparatus 100 includes an arthroscope 101 that is an endoscope. The arthroscope 101 includes an inserting section (an arthroscope inserting section) 102 and a holding section (an arthroscope holding section) 103. In a treatment in which the treatment system 1 is used, a distal portion of the inserting section 102 is inserted into a joint cavity S. The holding section 103 is connected to one end of a universal cord 105. The other end of the universal cord 105 is connected to an image processing unit 106 such as an image processor. The image processing unit 106 is electrically connected to a display unit 107 such as a monitor.

In the distal portion of the inserting portion 102, an imaging element 108 is disposed. The imaging element 108 is configured to image a subject through an observation window (not shown). The imaging element 108 is electrically connected to the image processing unit 106 via an imaging cable (not shown) extended through an inside of the inserting portion 102, an inside of the holding portion 103 and an inside of the universal cord 105. An image of the imaged subject is subjected to image processing by the image processing unit 106. Further, the subject image subjected to the image processing is displayed in the display unit 107. It is to be noted that in the arthroscope apparatus 100, a light source unit (not shown) is provided, and the subject is irradiated with light emitted from the light source unit.

The ultrasonic treatment apparatus 2 includes an ultrasonic treatment instrument (a hand piece) 3 and an electric power source unit 6. The electric power source unit 6 includes an electric power source, a control section formed of a CPU (a central processing unit) or an ASIC (an application specific integrated circuit), and a storage section such as a memory. The ultrasonic treatment instrument 3 has a longitudinal axis C. Here, one of two directions parallel to the longitudinal axis C is a distal direction (a direction of an arrow C1 of FIG. 1), and an opposite direction to the distal direction is a proximal direction (a direction of an arrow C2 of FIG. 1). The ultrasonic treatment instrument 3 includes a transducer unit 11, a holding unit 12, a sheath 13, and an ultrasonic probe 15. The vibrator unit 11 is connected to one end of a cable 5. The other end of the cable 5 is connected to the electric power source unit 6.

The holding unit 12 includes a cylindrical holding case 17 extended along the longitudinal axis C. The transducer unit 11 is inserted into the holding case 17 from a proximal side, and the sheath 13 is inserted into the holding case 17 from a distal side. Further, inside the holding case 17, the oscillator unit 11 is coupled with the sheath 13. Additionally, the ultrasonic probe 15 is inserted through the sheath 13. The ultrasonic probe 15 is coupled with the transducer unit 11 inside the holding case 17. To the holding case 17, there is attached an energy operation input button 18 that is an energy operation input portion. Additionally, the ultrasonic probe 15 projects from a distal end of the sheath 13 toward the distal side.

FIG. 2 is a view showing a constitution of the transducer unit 11. As shown in FIG. 2, the transducer unit 11 includes a transducer case 21 and an ultrasonic transducer 22 that is a vibration generating portion to be disposed inside the vibrator case 21. The vibrator case 21 is coupled with the sheath 13. In the ultrasonic vibrator 22, there are (four in the present embodiment) piezoelectric elements 23A to 23D configured to change a current into an ultrasonic vibration. The ultrasonic transducer 22 is connected to one end of each of electric wires 25A and 255. The electric wires 25A and 25B are extended through the inside of the cable 5, and their other ends are connected to the electric power source unit 6. An electric power is supplied from the electric power source unit 6 to the ultrasonic transducer 22 via the electric wires 25A and 25B, thereby generating the ultrasonic vibration in the ultrasonic oscillator 22.

Additionally, the transducer unit 11 includes a horn member 26. The ultrasonic transducer 22 is attached to the horn member 26, and the horn member 26 is supported by the transducer case 21. The ultrasonic vibration generated in the ultrasonic vibrator 22 is transmitted to the horn member 26. In the horn member 26, a cross section changing portion 27 is provided in which a cross section perpendicular to the longitudinal axis C decreases toward the distal direction. An amplitude of the ultrasonic vibration is enlarged by the cross section changing portion 27. In a distal portion of the horn member 26, an internal thread portion 28A is provided. Further, in a proximal portion of the ultrasonic probe 15, an external thread portion 28B is provided. When the external thread portion 28B is screwed into the internal thread portion 28A, the ultrasonic probe 15 is connected to the horn member 26. Consequently, the ultrasonic probe 15 is coupled with the transducer unit 11.

FIG. 3 is a view showing a constitution of the ultrasonic probe 15. As shown in FIG. 3, the ultrasonic probe 15 includes a probe main body 31 extended along the longitudinal axis C, and a treating section 32 provided on a distal side with respect to the probe main body 31. The treating section 32 includes an exposed surface (an exposed face) 34 exposed to the outside. The ultrasonic vibration generated in the ultrasonic transducer 22 is transmitted to the probe main body 31 of the ultrasonic probe 15 via the horn member 26. Further, in the probe main body 31, the ultrasonic vibration is transmitted from the proximal side toward the distal side. The treating section 32 treats a treated object by use of the ultrasonic vibration transmitted via the probe main body 31. It is to be noted that the ultrasonic vibration is transmitted from the proximal direction toward the distal direction, and hence the distal direction becomes a transmitting direction of the ultrasonic vibration. Additionally, in the present embodiment, the ultrasonic probe 15 (the probe main body 31 and the treating section 32) performs a longitudinal vibration in a vibrating direction that is parallel to the distal side and the proximal side in a state where the ultrasonic vibration is transmitted.

FIG. 4 is a view showing a constitution of the treating section 32. Here, one of directions perpendicular to the longitudinal axis C is defined as a first perpendicular direction (a direction of an arrow P1 of FIG. 4), and an opposite direction to the first perpendicular direction is defined as a second perpendicular direction (a direction of an arrow P2 of FIG. 4). As shown in FIG. 4, the treating section 32 includes a rake portion 33 that is a curved projecting portion shaped in the form of a rake. The rake portion 33 is curved with respect to the longitudinal axis C toward the first perpendicular direction. Consequently, the rake portion 33 projects toward the first perpendicular direction. The exposed surface 34 of the treating section 32 includes a projecting end face 35 that is a projecting end of the rake portion 33 (an end on a first perpendicular direction side). The projecting end face 35 becomes a contact portion configured to be brought into contact with the treated object in the treatment. The projecting end face 35 is positioned on the first perpendicular direction side with respect to the longitudinal axis C. Further, the projecting end face 35 that is the projecting end of the rake portion 33 is a first-perpendicular-direction-side end of the rake portion 33.

Here, two directions perpendicular to the longitudinal axis C and perpendicular to the first perpendicular direction and the second perpendicular direction are defined as a third perpendicular direction (a direction of an arrow P3 of FIG. 4) and a fourth perpendicular direction (a direction of an arrow P4 of FIG. 4). The exposed surface 34 of the treating section 32 includes a first curved exposed portion 36 facing in the distal direction in the rake portion (the curved projecting portion) 33, a second curved exposed portion 37 facing in the proximal direction in the rake portion 33, a third curved exposed portion 38 directed in the third perpendicular direction in the rake portion 33, and a fourth curved exposed portion 39 facing toward the fourth perpendicular direction in the rake portion 33. A distal end of the treating section 32 (a distal end of the ultrasonic probe 15) is formed by the first curved exposed portion 36. The first curved exposed portion 36, the second curved exposed portion 37, the third curved exposed portion 38 and the fourth curved exposed portion 39 are extended from the projecting end face 35, which is the contact portion, toward a second perpendicular direction side.

On the first curved exposed portion 36 and the third curved exposed portion 38, an index portion 40 is provided. The index portion 40 includes plural (four in the present embodiment) index surfaces 41A1 to 41A4 disposed on the first curved exposed portion 36, and plural (four in the present embodiment) index surfaces 41C1 to 41C4 disposed on the third curved exposed portion 38. In the first curved exposed portion 36, the index surfaces 41A1 to 41A4 are continuously arranged in the first perpendicular direction and the second perpendicular direction, and in the third curved exposed portion 38, the index surfaces 41C1 to 41C4 are continuously arranged in the first perpendicular direction and the second perpendicular direction. In the first curved exposed portion 36, the index surfaces 41A1 to 41A4 are arranged from the projecting end face 35 toward the second perpendicular direction side in order of the index surfaces 41A1, 41A2, 41A3, and 41A4, and in the third curved exposed portion 38, the index surfaces 41C1 to 41C4 are arranged from the projecting end face 35 toward the second perpendicular direction side in order of the index surfaces 41C1, 41C2, 41C3, and 41C4.

As described above, the index surfaces 41A1 to 41A4 and 41C1 to 41C4 are provided, whereby in the first curved exposed portion 36 and the third curved exposed portion 38 of the rake portion (the curved projecting portion) 33, the index portion 40 is formed in a part on the second perpendicular direction side with respect to the projecting end face 35. Additionally, the first curved exposed portion 36 is directed toward the distal direction that is one of directions perpendicular to the first perpendicular direction and the second perpendicular direction. Further, the third curved exposed portion 38 faces toward the third perpendicular direction that is one of the directions perpendicular to the first perpendicular direction and the second perpendicular direction. Therefore, the index portion 40 formed of the index surfaces 41A1 to 41A4 and 41C1 and 41C4 is disposed in a region facing toward one of the directions perpendicular to the first perpendicular direction and the second perpendicular direction, in the exposed surface 34 of the treating section 32.

In the first curved exposed portion 36, each of the index surfaces 41A1 to 41A4 has an angle relative to the first perpendicular direction which is different from the angle of the adjacent index surface (the corresponding surface in the surfaces 41A1 to 41A4). For example, the angle of the index surface 41A1 relative to the first perpendicular direction is 120°, and an angle of the index surface 41A2 relative to an intruding direction is 150°. Further, an angle of the index surface 41A3 with respect to the intruding direction is 0° (the index surface is parallel to the invading direction), and an angle of the index surface 41A4 relative to the intruding direction is 30°. The index surfaces 41A1 to 41A4 are formed as described above, and hence in the first curved exposed portion 36, each of ridgelines 42A1 to 42A3 is formed between each of the index surfaces 41A1 to 41A4 and the adjacent index surface (the corresponding surface in the surfaces 41A1 to 41A4). The ridgeline 42A1 is formed between the index surface 41A1 and the index surface 41A2, and the ridgeline 42A2 is formed between the index surface 41A2 and the index surface 41A3. Further, the ridgeline 42A3 is formed between the index surface 41A3 and the index surface 41A4. In the first curved exposed portion 36, the ridgelines 42A1 to 42A3 are extended along the third perpendicular direction and the fourth perpendicular direction. That is, the ridgelines 42A1 to 42A3 are extended in a state where the ridgelines intersect the first perpendicular direction and the second perpendicular direction. Each of the ridgelines 42A1 to 42A3 is away as much as a predetermined space (e.g., 0.4 mm to 0.7 mm) from the adjacent ridgeline (the corresponding line in the ridgelines 42A1 to 42A3) in the first perpendicular direction and the second perpendicular direction.

Additionally, also in the third curved exposed portion 38, each of the index surfaces 41C1 to 41C4 has an angle relative to the first perpendicular direction which is different from the angle of the adjacent index surface (the corresponding surface in the surfaces 41C1 to 41C4). Therefore, also in the third curved exposed portion 38, each of ridgelines 42C1 to 42C3 is formed between each of the index surfaces 41C1 to 41C4 and the adjacent index surface (the corresponding surface in the surfaces 41C1 to 41C4). In the third curved exposed portion 38, the ridgelines 42C1 to 42C3 are extended along the distal direction and the proximal direction. That is, the ridgelines 42C1 to 42C3 are extended in a state where the ridgelines transverse the first perpendicular direction and the second perpendicular direction. Each of the ridgelines 42C1 to 42C3 is away as much as a predetermined space (e.g., 0.4 mm to 0.7 mm) from the adjacent ridgeline (the corresponding line in the ridgelines 42C1 to 42C3) in the first perpendicular direction and the second perpendicular direction.

Next, a function and an effect of the ultrasonic probe 15 and the treatment system 1 of the present embodiment will be described. When the treatment is performed by using the treatment system 1 including the ultrasonic treatment apparatus 2, as shown in FIG. 1, the sheath 13 and the ultrasonic probe 15 of the ultrasonic treatment apparatus 2 are inserted into the joint cavity S. Additionally, the inserting section 102 of the arthroscope apparatus 100 is inserted into the joint cavity S. Further, for example, the bone 32 is resected as the treated object in the joint J by the treating section 32 of the ultrasonic probe 15.

When the bone B2 that is the treated object is resected, the projecting end face 35 as the contact portion is brought into contact with the bone B2. Further, the energy operation input button 18 is pressed, and an energy operation is input. In consequence, an operation signal is transmitted to the electric power source unit 6 via an electric signal line (not shown). Further, the electric power is output from the electric power source unit 6, and the output electric power is supplied to the ultrasonic transducer 22, thereby generating the ultrasonic vibration in the ultrasonic vibrator 22. The ultrasonic vibration generated in the ultrasonic transducer 22 is transmitted to the ultrasonic probe 15 via the horn member 26. Further, the ultrasonic vibration is transmitted from the proximal side toward the distal side in the probe main body 31 of the ultrasonic probe 15. Further, the treating section 32 performs a treatment to resect the bone B2 by use of the transmitted ultrasonic vibration. The probe main body 31 and the treating section 32, when the ultrasonic vibration is transmitted, perform the longitudinal vibration in the vibrating direction that is parallel to the proximal direction and the distal direction.

FIG. 5 is a view showing a state where the treated object (the bone B2) is resected with the treating section 32. As shown in FIG. 5, the treating section 32 performs the longitudinal vibration in a state where the projecting end face 35 of the treating section 32 is in contact with the bone B2, whereby the bone 52 is resected. When the bone B2 is cut, the rake portion 33 that is the curved projecting portion intrudes into the bone B2 from the projecting end face 35. That is, when the bone B2 is resected, the projecting end face 35 intrudes (moves) into the bone B2 toward the first perpendicular direction (the direction of the arrow P1 of FIG. 5). Here, a direction in which the projecting end face 35 of the contact portion intrudes (moves) into the treatment object (the bone B2), when the bone B2 of the treated object is resected, is defined as the intruding direction. In the present embodiment, the first perpendicular direction is defined as the intruding direction, and the second perpendicular direction (the direction of the arrow P2 of FIG. 5) is defined as an anti-intruding direction that is an opposite direction to the intruding direction. Therefore, the projecting end face 35 as the contact portion treats the treated object while intruding into the treated object in the intruding direction toward the inside of the treated object.

The directions are defined as described above, whereby the index portion 40 formed of the index surfaces 41A1 to 41A4 and 41C1 to 41C4 is disposed on an anti-intruding direction side (the second perpendicular direction side in the present embodiment) with respect to the projecting end face 35 that is the contact portion. Additionally, in the exposed surface 34 of the treating section 32, the index portion 40 is disposed in a region (the first curved exposed portion 36 and the third curved exposed portion 38 in the present embodiment) facing toward one of directions (the distal direction or the third perpendicular direction in the present embodiment) perpendicular to the intruding direction (the first perpendicular direction in the present embodiment) and the anti-intruding direction.

As shown in FIG. 5, in the treatment to resect the bone B2 of the treatment object, the bone B2 and the treating section 32 are imaged as subjects by the imaging element 108 provided in the inserting section 102 of the arthroscope 101. Consequently, the index portion 40 (the index surfaces 41A1 to 41A4 and 41C1 to 41C4 and the ridgelines 42A1 to 42A3 and 42C1 to 42C3) is imaged as the subject. Further, the subject image processed by the image processing unit 106 is displayed in the display unit 107.

Figure 6:
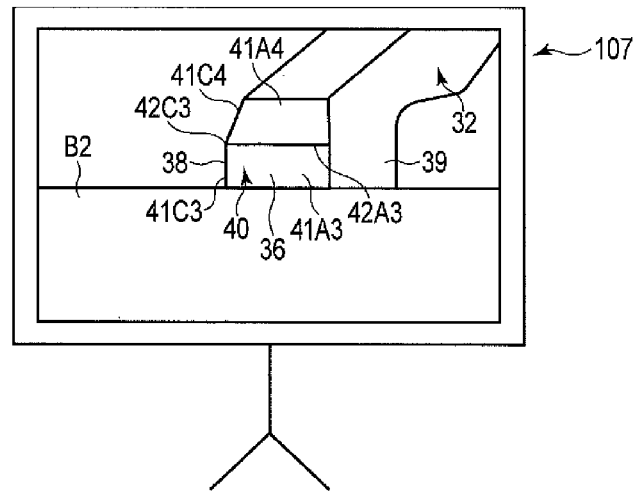
FIG. 6 is a schematic view showing one example of a subject image to be displayed in a display unit in the state where the treated object is resected with the treating section according to the first embodiment.
Figure 7:
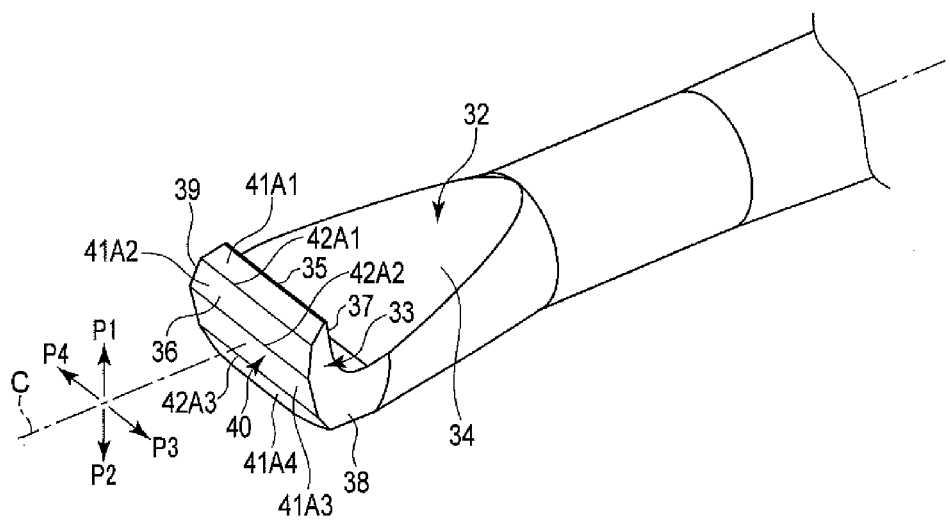
FIG. 7 is a perspective view schematically showing a constitution of a treating section of an ultrasonic probe according to a first modification of the first embodiment.

FIG. 6 is a view showing one example of the subject image to be displayed in the display unit 107 in the state where the treated object (the bone B2) is resected with the treating section 32. As shown in FIG. 6, in the subject image to be displayed in the display unit 107 in the state where the bone B2 is resected, the index portion 40 is displayed as the subject. An operator recognizes an intruding amount (a moving amount) of the projecting end face 35 as the contact portion into the treated object (the bone B2) toward the intruding direction (the first perpendicular direction in the present embodiment) on the basis of the index portion 40 to be displayed in the display unit 107. For example, in the one example shown in FIG. 6, the index surfaces 41A1, 41A2, 41C1 and 41C2 are positioned on an intruding direction side (the first perpendicular direction side) with respect to the surface of the bone B2, and the index surfaces 41A4 and 41C4 are positioned on an anti-intruding direction side (the second perpendicular direction side) with respect to the surface of the bone B2. Therefore, it is recognized that the projecting end face 35 intrudes into the bone B2 in the intruding direction up to a state where the index surface 41A3 and the index surface 41C3 are positioned on the surface of the bone B2. Further, the intruding amount (the moving amount) of the projecting end face 35 into the treated object (the bone B2) toward the invading direction (the first perpendicular direction in the present embodiment) is more accurately recognized from an area of the index surface 41A3 on the anti-intruding direction side with respect to the surface of the bone B2 and an area of the index surface 41C3 on the anti-intruding direction side with respect to the surface of the bone B2. That is, the intruding amount (the moving amount) of the projecting end face 35 into the bone B2 toward the intruding direction is more accurately recognized from a distance from the surface of the bone B2 to the ridgeline 42A3 and a distance from the surface of the bone B2 to the ridgeline 42C3. As described above, the index portion 40 is an index indicating the intruding amount (the moving amount) of the projecting end face 35 as the contact portion into the treated object toward the intruding direction.

Here, in the treatment to resect the treated object, a resecting depth of the treated object corresponds to the intruding amount of the projecting end face 35 that is the contact portion into the treated object toward the intruding direction. As described above, the intruding amount of the projecting end face 35 into the treated object (the bone B2) in the intruding direction is recognized, so that the operator can appropriately recognize the resecting depth of the treated object in the middle of the treatment to resect the treated object. Therefore, in the treatment to resect the treated object, the treated object is appropriately resected at a desirable resecting depth.

Additionally, the index surfaces 41A1 to 41A4 and 41C1 to 41C4 and the ridgelines 42A1 to 42A3 and 42C1 to 42C3 that form the index portion 40 are formed on the exposed surface 34 of the treating section 32 simultaneously when the treating section 32 is formed by casting or the like. Consequently, in manufacturing of the ultrasonic probe 15, after the treating section 32 is formed by the casting or the like, a step of forming the index portion 40 on the exposed surface 34 does not have to separately be performed. That is, after the treating section 32 is formed by the casting or the like, a step of applying color to the exposed surface 34 or performing a coating process to form the index portion (40) or a step of forming graduations as the index portion (40) on the exposed surface 34 by cutting does not have to be performed. In the present embodiment, the treating section 32 is formed by the casting or the like, and simultaneously, the index surfaces 41A1 to 41A4 and 41O1 to 41C4 and the ridgelines 42A1 to 42A3 and 42C1 to 42C3 are formed as the index portion 40 on the exposed surface 34 of the treating section 32, so that also in a case where the index portion 40 is provided on the ultrasonic probe 15 (the exposed surface 34 of the treating section 32), the ultrasonic probe 15 can easily be manufactured.

Modification of First Embodiment

It is to be noted that in the first embodiment, the index portion 40 (the index surfaces 41A1 to 41A4 and 4101 to 4104) is disposed in the first curved exposed portion 36 and the third curved exposed portion 38, but it is not limited to this example. For example, in a first modification of the first embodiment, as shown in FIG. an index portion 40 (index surfaces 41A1 to 41A4) may be disposed only in a first curved exposed portion 36. In the present modification, index surfaces 4101 to 41C4 and ridgelines 42C1 to 42C3 are not formed in a third curved exposed portion 38.

Additionally, in another modification, the index portion 40 is not provided in the first curved exposed portion 36 or the third curved exposed portion 38, and may be disposed only in a second curved exposed portion 37 and a fourth curved exposed portion 39. Further, in still another modification, the index portion 40 may be disposed only in the second curved exposed portion 37. That is, the index portion 40 (e.g., the index surfaces 41A1 to 41A4 in a case where the index portion is disposed in the first curved exposed portion) may be disposed in at least one of the first curved exposed portion 36, the second curved exposed portion 37, the third curved exposed portion 38, and the fourth curved exposed portion 39.

Figure 8:
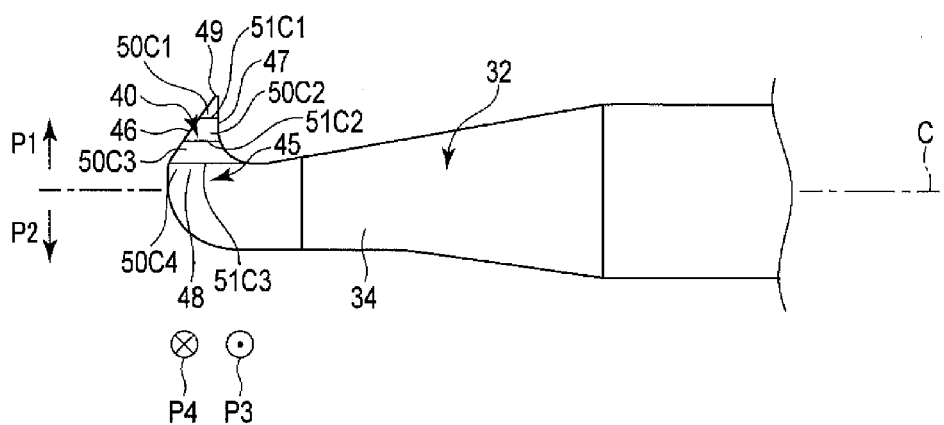
FIG. 8 is a schematic view showing a constitution of a treating section of an ultrasonic probe according to a second modification of the first embodiment.

Additionally, in a second modification of the first embodiment, as shown in FIG. 8, a hook portion 45 shaped in the form of a hook may be provided as a curved projecting portion in place of the rake portion 33. Similarly to the rake portion 33, the hook portion 45 is curved relative to a longitudinal axis C toward a first perpendicular direction (a direction of an arrow 21 of FIG. 8), and projects toward the first perpendicular direction. Further, in a projecting end of the hook portion 45 (an end on a first perpendicular direction side), a projecting end face 49 is provided as a contact portion. In the present modification, the projecting end face 49 becomes a contact portion to be brought into contact with a treated object in a treatment to resect the treated object (a bone). Additionally, an exposed surface 34 of a treating section 32 includes a first curved exposed portion 46 facing toward a distal direction in the hook portion 45, a second curved exposed portion 47 directed toward a proximal direction in the hook portion 45, a third curved exposed portion 48 facing in a third perpendicular direction 23 (a vertically upper direction relative to a paper surface in FIG. 8) in the hook portion 45, and a fourth curved exposed portion (not shown) facing toward a fourth perpendicular direction P4 (a vertically lower direction relative to the paper surface in FIG. 8) in the hook portion 45.

Also in the present modification, similarly to the first embodiment, the first perpendicular direction is defined as an intruding direction, and a second perpendicular direction is defined as an anti-intruding direction. In the present modification, an index portion 40 is disposed only in the third curved exposed portion 48, and the index portion 40 includes plural (four in the present modification) index surfaces 50C1 to 50C4. Further, each of ridgelines 51C1 to 51C3 is formed between each of the index surfaces 50C1 to 50C4 and an adjacent index surface (a corresponding surface in 50C1 to 50C4). Similarly to the ridgelines 42A1 to 42A3 and 42C1 to 42C3 of the first embodiment, the ridgelines 51C1 to 51C3 are extended in a state where the ridgelines intersect the intruding direction and the anti-intruding direction. Also in the present modification, the index portion 40 is positioned on an anti-intruding direction side (a second perpendicular direction side) with respect to the projecting end face 49 as the contact portion. Therefore, also in the present modification, the index portion 40 becomes an index indicating an intruding amount (a moving amount) of the projecting end face 49 as the contact portion into the treated object toward the intruding direction (the first perpendicular direction).

In the abovementioned first embodiment and the modifications of the first embodiment, the treating section (32) includes the curved projecting portion (33; 45) which is curved relative to the longitudinal axis (C) toward the first perpendicular direction (P1) that is the intruding direction, thereby projecting toward the first perpendicular direction (21). The distal end of the treating section (32) is formed by the curved projecting portion (33; 45). Further, the contact portion (35; 49) to be brought into contact with the treated object in the treatment to resect the treated object is positioned at a projecting end that is an end on the first perpendicular direction (P1) side of the curved projecting portion (33; 45). Further, the index portion (40) is disposed on the anti-intruding direction side (the second perpendicular direction (P2) side) with respect to the projecting end.

Second Embodiment

Next, a second embodiment of the present invention will be described with reference to FIG. 9. In the second embodiment, the constitution of the first embodiment is modified as follows. It is to be noted that the same components as in the first embodiment are denoted with the same reference signs, and the description is omitted.

Figure 9:
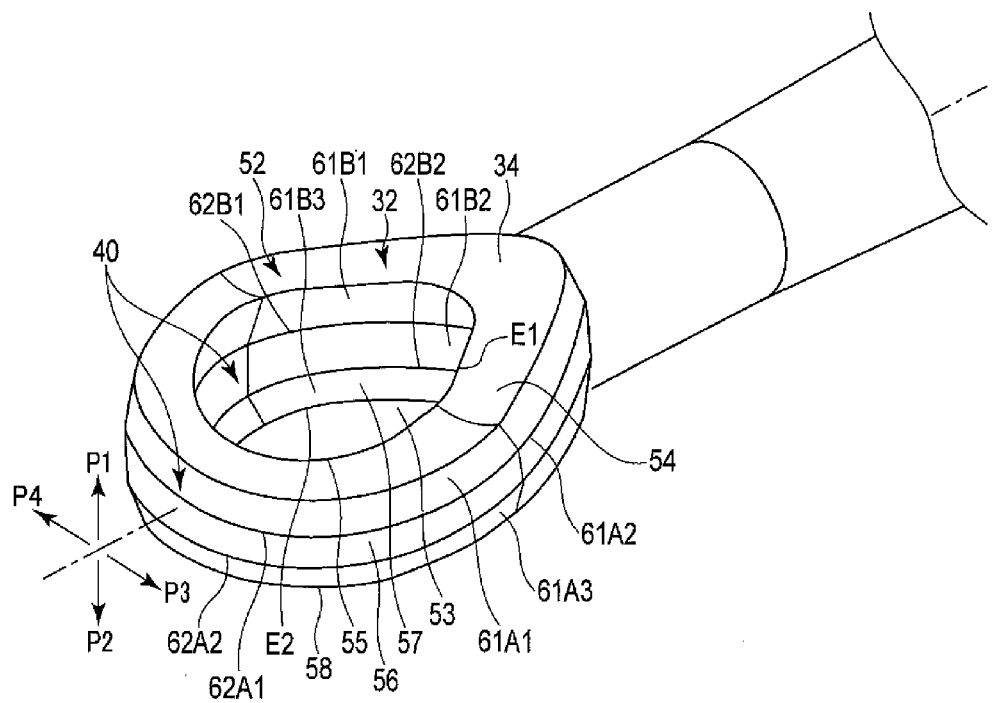
FIG. 9 is a perspective view schematically showing a constitution of a treating section of an ultrasonic probe according to a second embodiment.

FIG. 9 is a view showing a treating section 32 of an ultrasonic probe 15 of the present embodiment. As shown in FIG. 9, the treating section 32 includes a curette portion 52. In the present embodiment, the treating section 32 is extended along a longitudinal axis C without being curved. An exposed surface 34 of the treating section 32 includes a first outer periphery exposed portion 54 facing toward a first perpendicular direction (a direction of an arrow P1 of FIG. 9) in an outer periphery of the treating section 32, and a second outer periphery exposed portion 58 facing toward a second vertical direction (a direction of an arrow P2 of FIG. 9) in the outer periphery of the treating section 32. In the curette portion 52, an opening hole 53 is defined by a hole defining surface 57. The opening hole 53 opens at a first opening end E1 positioned on the first outer periphery exposed portion 54. Further, the hole defining surface 57 is extended from the first opening end E1 toward the second perpendicular direction.

In an edge portion of the first opening end E1 of the opening hole 53, an opening end blade portion 55 is provided. In a treatment to resect a treated object (a bone) by an ultrasonic vibration, the opening end blade portion 55 becomes a contact portion to be brought into contact with the treated object. The opening end blade portion 55 is positioned on a first perpendicular direction side with respect to the longitudinal axis C. The opening hole 53 opens at a second opening end E2 positioned in the second outer periphery exposed portion 58. Therefore, the opening hole 53 penetrates through the curette portion 52 of the treating section 32 along the first perpendicular direction and the second perpendicular direction between the first opening end E1 and the second opening end E2. The opening hole 53 penetrates the curette portion 52, thereby exposing the hole defining surface 57 to the outside of the treating section 32. Therefore, in the present embodiment, the hole defining surface 57 becomes a part of the exposed surface 34 of the treating section 32.

Additionally, in the outer periphery of the treating section 32, there is disposed an outer periphery relay portion 56 extended continuously along the first perpendicular direction and the second perpendicular direction between the first outer periphery exposed portion 54 and the second outer periphery exposed portion 58. A distal end of the treating section 32 is formed by the outer periphery relay portion 56. The outer periphery relay portion 56 becomes a part of the exposed surface 34 of the treating section 32. Additionally, in the opening hole 53, the hole defining surface 57 is extended continuously along the first perpendicular direction and the second perpendicular direction between the first outer periphery exposed portion 54 and the second outer periphery exposed portion 58.

It is to be noted that in the present embodiment, a region (e.g., the first outer periphery exposed portion 54, the second outer periphery exposed portion 58 and the outer periphery relay portion 56) other than the hole defining surface 57 in the exposed surface 34 of the treating section 32 becomes the outer periphery of the treating section 32. Further, the outer periphery relay portion 56 and the hole defining surface 57 become a relay exposed portion extended continuously along the first perpendicular direction and the second perpendicular direction between the first outer periphery exposed portion 54 and the second outer periphery exposed portion 58. Further, the relay exposed portion (56, 57) includes the outer periphery relay portion 56 that is an outer relay portion positioned in an outside of the opening hole 53, and the hole defining surface 57 that is an inner relay portion positioned in an inside of the opening hole 53. Further, the relay exposed portion (56, 57) becomes a part of the exposed surface 34 of the treating section 32.

In the present embodiment, the treating section 32 performs a longitudinal vibration by the ultrasonic vibration in a state where the opening end blade portion 55 that is a contact portion is in contact with the treated object, thereby resecting the treatment object (the bone). In consequence, the first outer periphery exposed portion (the opening end blade portion 55) first intrudes into the treated object. That is, when the treated object (the bone) is resected, the opening end blade portion 55 moves relative to the treated object toward the first perpendicular direction. Consequently, also in the present embodiment, the first perpendicular direction is defined as an intruding direction in which the opening end blade portion 55 as the contact portion intrudes into the treated object when the treated object is resected. Further, the second perpendicular direction is defined as an anti-intruding direction that is an opposite direction to the intruding direction.

In the present embodiment, index portions 40 are disposed in the outer periphery relay portion 56 and the hole defining surface 57. That is, the index portions 40 are disposed on the relay exposed portions (56, 57). The index portions 40 are disposed in the relay exposed portions (56, 57), and hence, in the exposed surface 34 of the treating section 32, the index portions 40 are positioned in a region facing toward one of directions perpendicular to the intruding direction (the first perpendicular direction) and the anti-intruding direction (the second perpendicular direction). Additionally, the index portions 40 are positioned on an anti-intruding direction side (a second perpendicular direction side) with respect to the opening end blade portion 55 as the contact portion.

The index portions 40 includes index surfaces 61A1 to 61A3 disposed in the outer periphery relay portion 56, and index surfaces 61B1 to 61B3 provided in the hole defining surface 57. In the outer periphery relay portion 56, each of the index surfaces 61A1 to 61A3 has an angle relative to the first perpendicular direction (the intruding direction) which is different from the angle of the adjacent index surface (the corresponding surface in the surfaces 61A1 to 61A3). Consequently, on the outer periphery relay portion 56, each of ridgelines 62A1 and 62A2 is formed between each of the index surfaces 61A1 to 61A3 and the adjacent index surface (the corresponding surface in the surfaces 61A1 to 61A3). Additionally, in the hole defining surface 57, each of the index surfaces 61B1 to 61B3 has an angle relative to the first perpendicular direction (the intruding direction) which is different from the angle of the adjacent index surface (the corresponding surface in the surfaces 61B1 to 61B3). Consequently, on the hole defining surface 57, each of ridgelines 62B1 and 62B2 is formed between each of the index surfaces 61B1 to 61B3 and the adjacent index surface (the corresponding surface in the surfaces 61B1 to 61B3). Similarly to the ridgelines 42A1 to 42A3 and 42C1 to 42C3, the ridgelines 62A1, 62A2, 62B1 and 62B2 are extended in a state where the ridgelines orthogonal to the intruding direction (the first perpendicular direction) and the anti-intruding direction (the second perpendicular direction). The index portions 40 are formed as described above, and hence the index portions 40 (the index surfaces 61A1 to 61A3 and 61B1 to 61B3 and the ridgelines 62A1, 62A2, 62B1 and 62B2) become an index indicating an intruding amount (a moving amount) of the opening end blade portion 55 as the contact portion into the treated object toward the intruding direction. Consequently, in the treatment to resect the treated object, the intruding amount of the opening end blade portion 55 as the contact portion into the treated object in the intruding direction is recognized by a surgeon. In consequence, the operator can appropriately recognize a resecting depth of the treated object in the middle of the treatment to resect the treated object.

Additionally, also in the present embodiment, the index surfaces 61A1 to 61A3 and 61B1 to 61B3 and the ridgelines 62A1, 62A2, 62B1 and 62B2 that form the index portions 40 are formed on the exposed surface 34 of the treating section 32 simultaneously when the treating section 32 is formed by casting or the like. Consequently, in manufacturing of the ultrasonic probe 15, after the treating section 32 is formed by the casting or the like, a step of forming the index portions 40 in the exposed surface 34 does not have to be separately performed. Therefore, even in a case where the index portions 40 are provided in the ultrasonic probe 15 (the exposed surface 34 of the treating section 32), the ultrasonic probe 15 can easily be manufactured.

Modification of Second Embodiment

It is to be noted that in the second embodiment, the index portions 40 are disposed in both the outer periphery relay portion 56 that is the outer relay portion and the hole defining surface 57 that is the inner relay portion, but it is not limited to this example. For example, as a modification, the index portion 40 may be disposed only in the outer periphery relay portion 56 or the hole defining surface 57.

Figure 10:
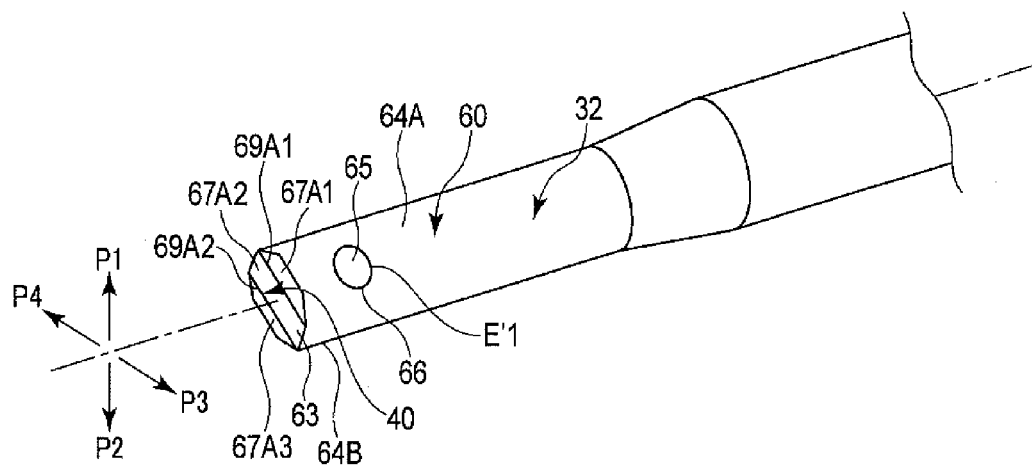
FIG. 10 is a perspective view schematically showing a constitution of a treating section of an ultrasonic probe according to a first modification of the second embodiment.
Figure 11:
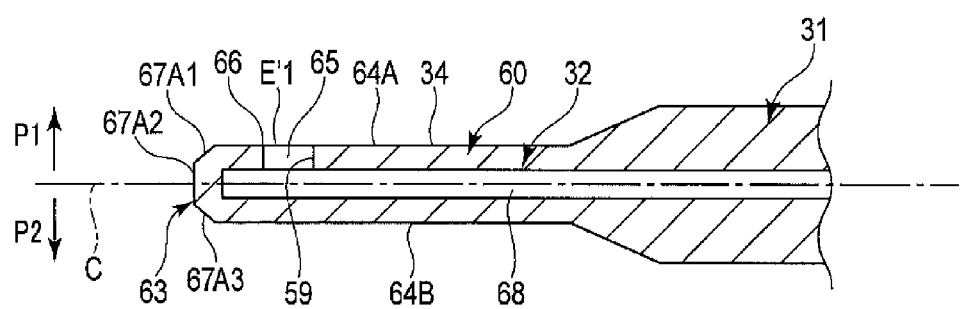
FIG. 11 is a cross-sectional view schematically showing the constitution of the ultrasonic probe according to the first modification of the second embodiment in a cross section parallel to a longitudinal axis.

Additionally, in a first modification of the second embodiment, as shown in FIG. 10 and FIG. 11, a pipe portion 60 may be formed in a treating section 32 in place of the curette portion 52. Also in the present modification, similarly to the second embodiment, an exposed surface 34 of the treating section 32 includes a first outer periphery exposed portion 64A facing toward a first perpendicular direction (a direction of an arrow P1 of FIG. 10) in an outer periphery of the treating section 32, and a second outer periphery exposed portion 64B facing toward a second perpendicular direction (a direction of an arrow P2 of FIG. 10) in the outer periphery of the treating section 32. Further, an opening hole 65 is defined by a hole defining surface 59, and the opening hole 65 opens at an opening end (a first opening end) E'1 positioned on the first outer periphery exposed portion 64A. Further, an opening end blade portion 66 that is a contact portion is provided in an edge portion of the opening end E'1 of the opening hole 65.

However, in the present modification, the opening hole 65 opens only at the opening end E'1 of the first outer periphery exposed portion 64A, and does not open to the outside of the treating section 32 in the second outer periphery exposed portion 64B. Thus, the opening hole 65 does not penetrate the pipe portion 60 in the first perpendicular direction and the second perpendicular direction. Consequently, differently from the second embodiment, the hole defining surface 59 is not exposed to an outside of the treating section 32, and is not included in the exposed surface 34 of the treating section 32.

Additionally, in the present modification, the exposed surface 34 includes a distal end exposed portion 63 that forms a distal end of the treating section 32. The distal end exposed portion 63 faces toward a distal direction perpendicular to the first perpendicular direction and the second perpendicular direction. The distal end exposed portion 63 becomes a relay exposed portion extended continuously along the first perpendicular direction and the second perpendicular direction between the first outer periphery exposed portion 64A and the second outer periphery exposed portion 64B. A dimension of the distal end exposed portion 63 in the first perpendicular direction and the second perpendicular direction is larger than a dimension of the distal end exposed portion in a third perpendicular direction (a direction of an arrow P3 of FIG. 10) and a fourth perpendicular direction (a direction of an arrow P4 of FIG. 10).

Additionally, in the present modification, a passage 68 that is extended through an inside of a probe main body 31 along a longitudinal axis C is formed in an ultrasonic probe 15. Inside the pipe portion 60 of the treating section 32, the passage 68 communicates with the opening hole 65. When a treated object (a bone) is resected by using an ultrasonic vibration, the opening end blade portion 66 as the contact portion intrudes into the treated object toward the first perpendicular direction. Therefore, also in the present modification, the first perpendicular direction is defined as an intruding direction, and the second perpendicular direction is defined as an anti-intruding direction. The resected bone is sucked and collected by a suction unit (not shown) via the opening hole 65 and the passage 68.

In the present modification, an index portion 40 is disposed in a distal end exposed portion 63 that is a relay exposed portion. The index portion 40 includes index surfaces 67A1 to 67A3. Each of the index surfaces 67A1 to 67A3 has an angle relative to the first perpendicular direction (the intruding direction) which is different from the angle of the adjacent index surface (the corresponding surface in the surfaces 67A1 to 67A3). Thus, in the distal end exposed portion 63, each of ridgelines 69A1 and 69A2 is formed between each of the index surfaces 67A1 to 67A3 and the adjacent index surface (the corresponding surface in the surfaces 67A1 to 67A3). The ridgelines 69A1 and 69A2 are extended in a state where the ridgelines intersect the intruding direction and the anti-intruding direction in the same manner as in the ridgelines 42A1 to 42A3 and 42C1 to 42C3 of the first embodiment. Also in the present modification, the index portion 40 is positioned on an anti-intruding direction side (a second perpendicular direction side) with respect to the opening end blade portion 66 as the contact portion. Therefore, also in the present modification, the index portion 40 becomes an index indicating an intruding amount (a moving amount) of the opening end blade portion 66 as the contact portion into the treated object toward the intruding direction (the first perpendicular direction).

In the abovementioned second embodiment and its modification, the exposed surface (34) includes the first outer periphery exposed portion (54; 64A) facing toward the first perpendicular direction (P1) in the outer periphery of the treating section (32), the second outer periphery exposed portion (58; 64B) facing toward the second perpendicular direction (P2) in the outer periphery of the treating section (32), and the relay exposed portion (56, 57; 63) extended continuously along the first perpendicular direction (P1) and the second perpendicular direction (P2) between the first outer periphery exposed portion (54; 64A) and the second outer periphery exposed portion (58; 64B). Further, in the treating section (32), there is formed the opening hole (53; 65) opened at the first opening end (E1; E'1) of the first outer periphery exposed portion (54; 64A). Further, the contact portion (55; 66) to be brought into contact with the treated object in the treatment to resect the treated object is positioned at the first opening end (E1; E'1). Further, the index portion (40) is disposed in the relay exposed portion (56, 57; 63).

Modifications of First Embodiment and Second Embodiment

In the first embodiment, the second embodiment and their modifications, the contact portion (35; 49; 55; 66) to be brought into contact with the treated object in the treatment to resect the treated object is positioned on the first perpendicular direction (P1) side with respect to the longitudinal axis C. Further, the intruding direction of the contact portion (35; 49; 55; 66) in the state where the treated object is resected matches the first perpendicular direction (P1). Further, the index portion (40) is disposed on the anti-intruding direction side (the second perpendicular direction (P2) side) with respect to the contact portion (35; 49; 55: 66).

Third Embodiment

Next, a third embodiment of the present invention will be described with reference to FIG. 12 and FIG. 13. In the third embodiment, the constitution of the first embodiment is modified as follows. It is to be noted that the same components as in the first embodiment are denoted with the same reference signs, and the description is omitted.

Figure 12:
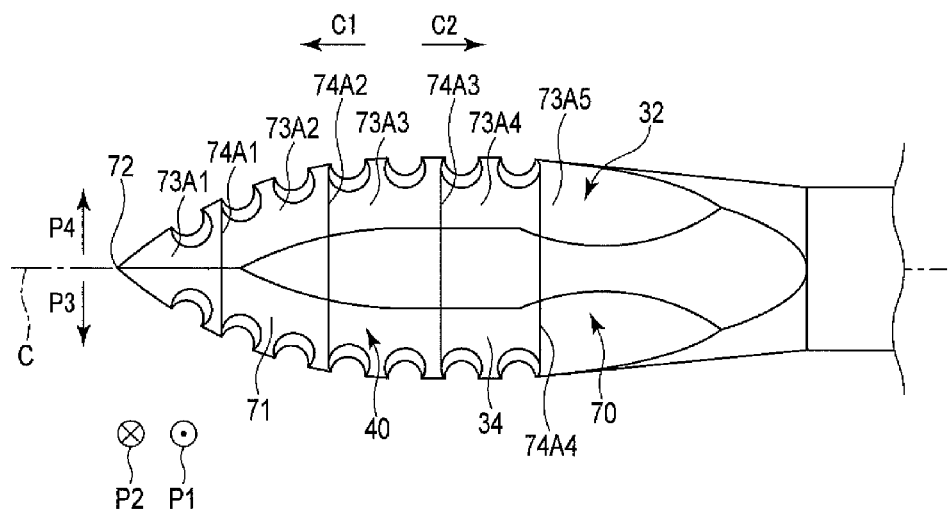
FIG. 12 is a schematic view showing a constitution of a treating section of an ultrasonic probe according to a third embodiment.
Figure 13:
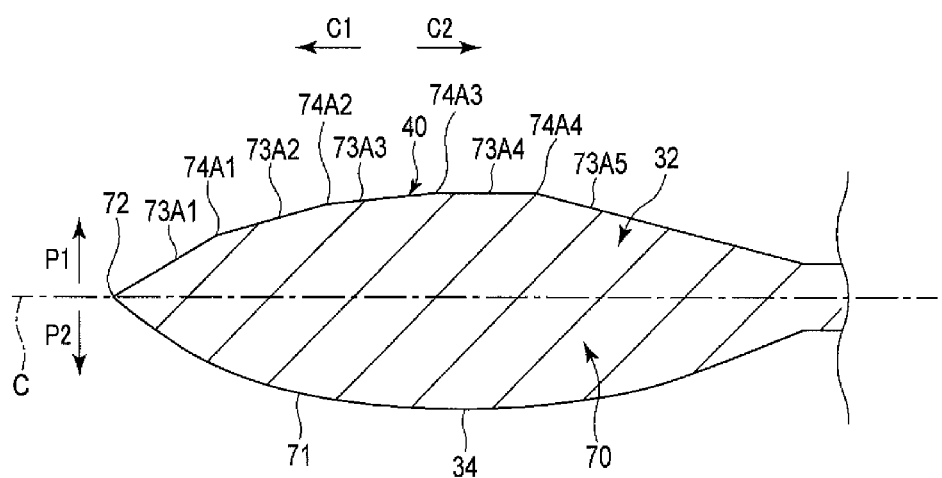
FIG. 13 is a cross-sectional view schematically showing the constitution of the treating section of the ultrasonic probe according to the third embodiment in a cross section parallel to a longitudinal axis.

FIG. 12 and FIG. 13 are views showing a treating section 32 of an ultrasonic probe 15 of the present embodiment. As shown in FIG. 12 and FIG. 13, the treating section 32 includes a blade portion 70. In the present embodiment, the treating section 32 is extended along a longitudinal axis C without being curved. A dimension of the blade portion 70 in a first perpendicular direction (a vertically upper direction relative to a paper surface in FIG. 12 and a direction of an arrow P1 of FIG. 13) and a second perpendicular direction (a vertically lower direction relative to the paper surface in FIG. 12 and a direction of an arrow P2 of FIG. 13) decreases, and a dimension of the blade portion in a third perpendicular direction (a direction of an arrow P3 of FIG. 12) and a fourth perpendicular direction (a direction of an arrow P4 of FIG. 12) increases.

An exposed surface 34 of the treating section 32 includes a sharp distal end narrowing portion 72, and an outer periphery exposed portion 71 extended from the distal end narrowing portion 72 toward a proximal direction (C2) in an outer periphery of the treating section 32. A distal end of the treating section 32 is formed by the distal end narrowing portion 72. Additionally, the distal end narrowing portion 72 is a contact portion to be brought into contact with a treated object in a treatment to resect the treated object by use of an ultrasonic vibration. Here, two directions that are a clockwise direction and a counterclockwise direction around the longitudinal axis C are defined as periaxial directions of the longitudinal axis. In the present embodiment, the outer periphery exposed portion 71 is extended along the whole periphery in the periaxial direction of the longitudinal axis. Therefore, in the outer periphery exposed portion 71, the exposed surface 34 of the treating section 32 faces toward one of directions perpendicular to the longitudinal axis C.

In the present embodiment, the treating section 32 performs a longitudinal vibration by the ultrasonic vibration in a state where the distal end narrowing portion 72 that is a contact portion is in contact with the treated object, thereby intruding into the treated object from the distal end narrowing portion 72. That is, the distal end narrowing portion 72 moves relative to the treatment object toward a distal direction. Thus, in the present embodiment, differently from the abovementioned embodiments, the distal direction (C1) is defined as an intruding direction in which the distal end narrowing portion 72 as the contact portion intrudes (moves) into the treated object when the treating section 32 intrudes into the treated object. Further, the proximal direction will be defined as an anti-intruding direction that is an opposite direction to the intruding direction.

In the present embodiment, an index portion 40 is disposed in the outer periphery exposed portion 71. The index portion 40 may be disposed along the whole periphery in the periaxial direction of the longitudinal axis, or may be disposed along a partial range in the periaxial direction of the longitudinal axis. In the present embodiment, the index portion 40 is formed only in a region of the outer periphery exposed portion 71 which faces toward the first perpendicular direction. The index portion 40 is disposed on the outer periphery exposed portion 71, and hence the index portion 40 is positioned in a region directed in one of directions perpendicular to the intruding direction (the distal direction) and the anti-intruding direction (the proximal direction) in the exposed surface 34 of the treating section 32. Additionally, the index portion 40 is disposed on an anti-intruding direction side (a proximal direction side) with respect to the distal end narrowing portion 72 as the contact portion.

The index portion 40 includes index surfaces 73A1 to 73A5. Each of the index surfaces 73A1 to 73A5 has an angle relative to the distal direction (the intruding direction) which is different from the angle of the adjacent index surface (the corresponding surface in the surfaces 73A1 to 73A5). Thus, in the outer periphery exposed portion 71, each of ridgelines 74A1 to 74A4 is formed between each of the index surfaces 73A1 to 73A5 and the adjacent index surface (the corresponding surface in the surfaces 73A1 to 73A5). The ridgelines 74A1 to 74A4 are extended in a state where the ridgelines intersect the intruding direction (the distal direction in the present embodiment) and the anti-intruding direction (the proximal direction in the present embodiment) in the same manner as in the index lines 42A1 to 42A3 and 42C1 to 42C3 of the first embodiment. According to the abovementioned constitution, the index portion 40 becomes an index indicating an intruding amount (a moving amount) of the distal end narrowing portion 72 as the contact portion into the treated object toward the intruding direction. Consequently, in a treatment in which the treating section 32 intrudes into the treated object, the intruding amount of the distal end narrowing portion 72 as the contact portion into the treatment object toward the intruding direction is recognized by an operator. In consequence, the surgeon can appropriately recognize a resecting depth of the treated object in the middle of a treatment to resect the treated object.

Additionally, also in the present embodiment, the index surfaces 73A1 to 73A5 and the ridgelines 74A1 to 74A4 that form the index portion 40 are formed in the exposed surface 34 of the treating section 32 simultaneously when the treating section 32 is formed by casting or the like. Thus, in manufacturing of the ultrasonic probe 15, after the treating section 32 is formed by the casting or the like, a step of forming the index portion 40 on the exposed surface 34 does not have to be separately performed. Therefore, also in a case where the index portion 40 is disposed in the ultrasonic probe 15 (the exposed surface 34 of the treating section 32), the ultrasonic probe 15 can easily be manufactured.

Modification of Third Embodiment

In a first modification of the third embodiment, as shown in FIG. 14, a drill portion 75 may be formed in a treating section 32 in place of the blade portion 70. Also in the present modification, similarly to the third embodiment, an exposed surface 34 of the treating section 32 includes a sharp distal end narrowing portion 76, and an outer periphery exposed surface 79 extended from the distal end narrowing portion 76 toward a proximal direction in an outer periphery of the treating section 32. Further, the distal end narrowing portion 76 becomes a contact portion to be brought into contact with a treated object in a treatment to resect the treated object by use of an ultrasonic vibration.

However, in the present modification, a probe main body 31 and the treating section 32 do not perform a longitudinal vibration in a state where the ultrasonic vibration is transmitted, but perform a torsional vibration in a vibrating direction that is parallel to periaxial directions (a direction of an arrow R1 of FIG. 14 and a direction of an arrow R2) of the longitudinal axis. Therefore, in an ultrasonic transducer 22 (see FIG. 2), the ultrasonic vibration is generated so that the probe main body 31 and the treating section 32 perform the torsional vibration. Additionally, in the outer periphery exposed surface 79, a groove-like portion 78 is extended spirally about a longitudinal axis C.

The treating section 32 performs the torsional vibration by the ultrasonic vibration in a state where the distal end narrowing portion 76 as the contact portion is in contact with the treated object, thereby resecting the treated object (a bone). When the treating section 32 intrudes into the treated object (the bone), the distal end narrowing portion 76 moves relative to the treated object toward a distal direction. Thus, similarly to the third embodiment, the distal direction (C1) is defined as an intruding direction in which the distal end narrowing portion 76 as the contact portion intrudes (moves) into the treated object when the treated object is resected. Further, the proximal direction (C2) is defined as an anti-intruding direction that is an opposite direction to the intruding direction.

In the present modification, the index portion 40 is disposed in the outer periphery exposed surface 79. The index portion 40 includes index surfaces 77A1 to 77A5. Each of the index surfaces 77A1 to 77A5 has an angle relative to the distal direction (the intruding direction) which is different from the angle of the adjacent index surface (the corresponding surface in the surfaces 77A1 to 77A5). Thus, on the outer periphery exposed surface 79, each of ridgelines 80A1 to 80A4 is formed between each of the index surfaces 77A1 to 77A5 and the adjacent index surface (the corresponding surface in the surfaces 77A1 to 77A5). The ridgelines 80A1 to 80A4 are extended in a state where the ridgelines intersect the intruding direction and the anti-intruding direction in the same manner as in the ridgelines 42A1 to 42A3 and 42C1 to 42C3 of the first embodiment. Also in the present modification, the index portion 40 is positioned on an anti-intruding direction side (a proximal direction side) with respect to the distal end narrowing portion 76 as the contact portion. Therefore, also in the present modification, the index portion 40 becomes an index indicating an intruding amount (a moving amount) of the distal end narrowing portion 76 as the contact portion into the treated object toward the intruding direction (the distal direction).

In the third embodiment and its modification, the contact portion (72; 76) is positioned at the distal end of the treating section (32). Further, the intruding direction of the contact portion (72; 76) in the state where the treated object is resected matches the distal direction (C1). Further, the index portion (40) is disposed on the anti-intruding direction side (the proximal direction (C2) side) with respect to the contact portion (72; 76).

Another Modification

It is to be noted that in the abovementioned embodiments and modifications, it has been described that a bone is treated as a treated object, but needless to say, it is applicable to a cartilage or a soft tissue (e.g., a synovial membrane or the like) other than the bone as the treated object.

In the abovementioned embodiments and modifications, in the exposed surface (34) of the treating section (32) of the ultrasonic probe (15), there is provided the contact portion (35; 49; 55; 66; 72; 76) to be brought into contact with the treated object in the treatment to resect the treated object.

The contact portion (35; 49; 55; 66; 72; 76) treats the treated object by the ultrasonic vibration transmitted to the treating section (32) while intruding toward the intruding direction (P1; C1) that is toward the inside of the treatment object from the state where the contact portion is in contact with the treated object. Further, on the exposed surface (34) of the treating section (32), the index portion (40) is disposed on the anti-intruding direction (P2; C2) side with respect to the contact portion (35; 49; 55; 66; 72; 76). The index portion (40) becomes the index indicating the intruding amount of the contact portion (35; 49; 55; 66; 72; 76) into the treated object toward the intruding direction (P1; C1). Further, the index portion (40) includes the index surfaces (41A1 to 41A4, 41C1 to 41C4; 41A1 to 41A4; 50C1 to 50C4; 61A1 to 61A3, 61B1 to 61B3; 67A1 to 67A3; 73A1 to 73A5; 77A1 to 77A5) arranged in the intruding direction (P1; C1), and each of the index surfaces (41A1 to 41A4, 41C1 to 41C4; 41A1 to 41A4; 50C1 to 50C4; 61A1 to 61A3, 61B1 to 61B3; 67A1 to 67A3; 73A1 to 73A5; 77A1 to 77A5) has the angle relative to the intruding direction (P1; C1) which is different from the angle of the adjacent index surface.

Reference Examples

Additionally, there will be described a first reference example in which index lines 91A1 to 91A5 and 9101 to 9105 are provided as an index portion 40 in place of index surfaces as shown in FIG. 15. It is to be noted that in the present reference example, similarly to the first embodiment, a rake portion 33 is provided in a treating section 32, and the index portion 40 is disposed in the rake portion 33. In the present reference example, in a first curved exposed portion 36, the index lines 91A1 to 91A5 are extended along a third perpendicular direction (a direction of an arrow P3 of FIG. 15) and a fourth perpendicular direction (a direction of an arrow P4 of FIG. 15). Further, on a third curved exposed portion 38, the index lines 91C1 to 91C5 are extended along a distal direction and a proximal direction. That is, the index lines 91A1 to 91A5 and 91C1 to 91C5 are extended in a state where the index lines intersect a first perpendicular direction (a direction of an arrow P1 of FIG. 15) and a second perpendicular direction (a direction of an arrow P2 of FIG. 15). Each of the index lines 91A1 to 91A5 and 91C1 to 91C5 is away as much as a predetermined space (0.4 mm to 0.7 mm in the present reference example) from the adjacent index line in the first perpendicular direction and the second perpendicular direction.

Additionally, in a second reference example shown in FIG. 16, colored surfaces 92A1 to 92A4 and 92C1 to 92C4 are disposed as index portions 40 in place of index surfaces. It is to be noted that in the present reference example, similarly to the first embodiment, a rake portion 33 is provided in a treating section 32, and the index portion 40 is disposed in the rake portion 33. In the present reference example, plural (four in the present reference example) colored surfaces 92A1 to 92A4 are disposed in a first curved exposed portion 36, and plural (four in the present reference example) colored surfaces 92C1 to 92C4 are disposed on a third curved exposed portion 38. The index portion 40 is disposed on an anti-intruding direction side (a second perpendicular direction (P2) side) with respect to a projecting end face (a projecting end) 35 that is a contact portion in the first curved exposed portion 36 and the third curved exposed portion 38. In the first curved exposed portion 36, the colored surfaces 92A1 to 92A4 are arranged continuously in an intruding direction (a first perpendicular direction P1) and an anti-intruding direction (a second perpendicular direction P2), and in the third curved exposed portion 38, the colored surfaces 92C1 to 92C4 are arranged continuously in the intruding direction and the anti-intruding direction. Therefore, the colored surfaces 92A1 to 92A4 and 92C1 to 92C4 are disposed from the projecting end face 35 as the contact portion toward the anti-intruding direction.

Each of the colored surfaces 92A1 to 92A4 has a different color from the adjacent colored surface (the corresponding surface in the surfaces 92A1 to 92A4). Each of the colored surfaces 92C1 to 92C4 has a different color from the adjacent colored surface (the corresponding surface in the surfaces 92C1 to 92C4). For example, the colored surfaces 92A1 and 9201 are red, the colored surfaces 92A2 and 92C2 are green, the colored surfaces 92A3 and 92C3 are yellow, and the colored surfaces 92A4 and 92C4 are blue. The colored surfaces 92A1 to 92A4 and 92C1 to 92C4 are formed as described above, and hence the index portion 40 becomes an index indicating an intruding amount (a moving amount) of the projecting end face 35 as the contact portion into a treated object (a bone B2) toward the intruding direction (the first perpendicular direction).

Figure 17:
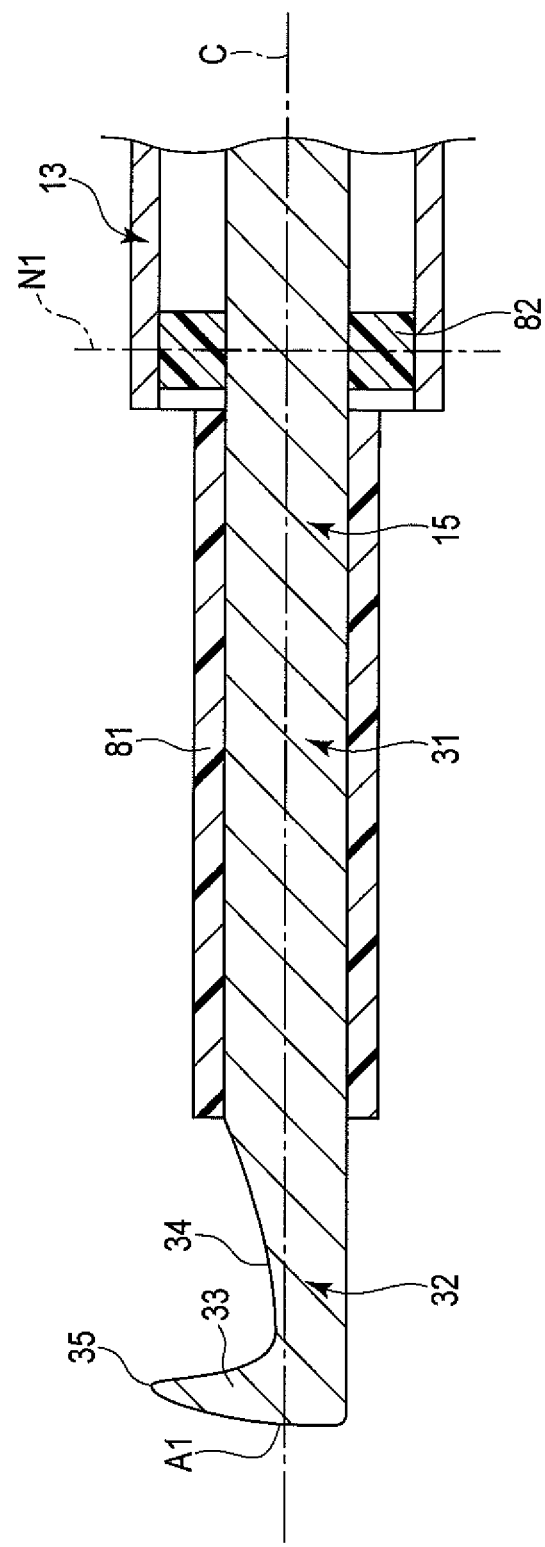
FIG. 17 is a schematic view showing a constitution of a distal portion of an ultrasonic treating instrument according to a third reference example.

Additionally, a third reference example shown in FIG. 17 will be described. FIG. 17 shows a constitution of a distal portion of an ultrasonic treatment instrument 3 of the present reference example. Also in the present reference example, similarly to the first embodiment, an ultrasonic probe 15 performs a longitudinal vibration in a vibrating direction that is parallel to a distal direction and a proximal direction in a state where an ultrasonic vibration is transmitted. In the ultrasonic probe 15, a distal end of a treating section 32 becomes an antinode position A1 of the ultrasonic vibration. Here, there is defined a node position N1 positioned most distally among node positions of the ultrasonic vibration. In the first embodiment, the sheath 13 that protects the ultrasonic probe 15 from the outside is extended up to the proximal end of the treating section 32 toward the distal direction. On the other hand, in the present reference example, a sheath 13 is extended only up to the vicinity of the node position N1 toward the distal direction. That is, in the first embodiment, the position of the proximal end of the treating section 32 in the direction parallel to the longitudinal axis C substantially matches the position of the distal end of the sheath 13, whereas in the present reference example, a proximal end of the treating section 32 is positioned on the distal direction side with respect to a distal end of the sheath 13.

Additionally, at the node position N1, a ring-shaped elastic member 82 is disposed between the sheath 13 and the ultrasonic probe 15. A space between the sheath 13 and the ultrasonic probe 15 is liquid-tightly kept by the elastic member 82. Consequently, inflow of a liquid from the distal side into the sheath 13 is effectively prevented.

Additionally, an outer surface of a probe main body 31 is covered with a thin tube member 81 between the node position N1 and the proximal end of the treating section 32 in the direction parallel to a longitudinal axis C. Therefore, a portion of the probe main body 31 which is not covered with the sheath 13 is also protected from the outside by the tube member 81. The portion is covered with the tube member 81 in place of the sheath 13, and hence a dimension of the ultrasonic treatment instrument 3 in a radial direction decreases between the distal end of the sheath 13 and the proximal end of the treating section 32. In consequence, the treating section 32 is easy to be inserted into a joint cavity S.

It is to be noted that in place of the tube member 81, coating may be applied to the outer surface of the probe main body 31 between the node position N1 and the proximal end of the treating section 32 in the direction parallel to the longitudinal axis C. Also in this case, the portion of the probe main body 31 which is not covered with the sheath 13 is also protected from the outside by the coating.

Additionally, in the present reference example, the distal end of the sheath 13 is positioned in the vicinity of the node position N1 positioned most distally, but it is not limited to this example. For example, the distal end of the sheath 13 may be positioned in the vicinity of a node position N2 positioned second distally. In this case, the outer surface of the probe main body 31 is covered with the tube member 81 between the node position N2 and the proximal end of the treating section 32 in the direction parallel to the longitudinal axis C. Further, at the node position N2, the elastic member (82) is disposed, and the space between the sheath 13 and the ultrasonic probe 15 is liquid-tightly kept. However, the node position N2 is positioned on the distal direction side with respect to a distal end of a holding unit 12.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An ultrasonic probe comprising:
a probe main body extended along a longitudinal axis, and configured to transmit an ultrasonic vibration from a proximal direction toward a distal direction; and
a treating section provided on a distal direction side with respect to the probe main body, and configured to perform a treatment of a treated object by use of the ultrasonic vibration transmitted via the probe main body,
the treating section including:
an exposed surface exposed to an outside;
a contact portion provided in the exposed surface, and configured to treat the treated object by the transmitted ultrasonic vibration while intruding into the treated object toward an intruding direction from a state where the contact portion is in contact with the treated object; and
an index portion which is disposed on an opposite direction side of the intruding direction with respect to the contact portion in the exposed surface, and which becomes an index indicating an intruding amount of the contact portion into the treated object toward the intruding direction, the index portion including index surfaces arranged in the intruding direction, each of the index surfaces having an angle relative to the intruding direction which is different from the angle of the adjacent index surface, wherein
in the index portion, a ridgeline is formed between each of the index surfaces and the adjacent index surface, and the adjacent ridgelines are parallel to each other, and
an angular difference between each of the index surfaces and the adjacent index surface is smaller than an angular difference between each of the index surfaces and an index surface that is adjacent to the adjacent index surface.

2. The ultrasonic probe of claim 1, wherein
the ridgelines are extended along a direction orthogonal to the intruding direction.

3. The ultrasonic probe of claim 1, wherein
the ridgelines are formed at equal intervals in the intruding direction.

4. The ultrasonic probe of claim 1, wherein
the index portion is disposed in a region facing toward one of directions perpendicular to the intruding direction in the exposed surface of the treating section.

5. The ultrasonic probe of claim 1, wherein
the contact portion is positioned at a distal end of the treating section,
the intruding direction of the contact portion matches the distal direction, and
the index portion is disposed on a proximal direction side with respect to the contact portion.

6. An ultrasonic treatment instrument comprising:
the ultrasonic probe of claim 1; and
a vibration generating portion provided on a proximal direction side with respect to the ultrasonic probe, and configured to generate the ultrasonic vibration to be transmitted to the ultrasonic probe.

7. A treatment system comprising:
the ultrasonic treatment instrument of claim 6;
an endoscope including an inserting section, the inserting section including an imaging element configured to image the treated object and the index portion of the treating section as subjects in the treatment of the treated object by the ultrasonic treatment instrument;
an image processing unit configured to perform image processing of an image of the subject imaged by the imaging element; and
a display unit in which the subject image subjected to the image processing by the image processing unit is configured to be displayed.

8. An ultrasonic probe comprising:
a probe main body extended along a longitudinal axis, and configured to transmit an ultrasonic vibration from a proximal direction toward a distal direction; and
a treating section provided on a distal direction side with respect to the probe main body, and configured to perform a treatment of a treated object by use of the ultrasonic vibration transmitted via the probe main body,
the treating section including:
  an exposed surface exposed to an outside;
  a contact portion provided in the exposed surface, and configured to treat the treated object by the transmitted ultrasonic vibration while intruding into the treated object toward an intruding direction from a state where the contact portion is in contact with the treated object; and
  an index portion which is disposed on an opposite direction side of the intruding direction with respect to the contact portion in the exposed surface, and which becomes an index indicating an intruding amount of the contact portion into the treated object toward the intruding direction, the index portion including index surfaces arranged in the intruding direction, each of the index surfaces having an angle relative to the intruding direction which is different from the angle of the adjacent index surface, wherein:
in the index portion, a ridgeline is formed between each of the index surfaces and the adjacent index surface, and the adjacent ridgelines are parallel to each other,
in a case where one of directions perpendicular to the longitudinal axis is defined as a first perpendicular direction and an opposite direction to the first perpendicular direction is defined as a second perpendicular direction, the contact portion is positioned on a first perpendicular direction side with respect to the longitudinal axis,
the intruding direction of the contact portion matches the first perpendicular direction, and
the index portion is disposed on a second perpendicular direction side with respect to the contact portion.

9. The ultrasonic probe of claim 8, wherein
the treating section includes a curved projecting portion which is curved relative to the longitudinal axis toward the first perpendicular direction, thereby projecting toward the first perpendicular direction,
the exposed surface of the treating section includes a first curved exposed portion which faces toward the distal direction in the curved projecting portion and forms a distal end of the treating section,
the contact portion is positioned at a projecting end which is an end of the curved projecting portion on the first perpendicular direction side, and
the index portion is disposed on the second perpendicular direction side with respect to the projecting end.

10. The ultrasonic probe of claim 9, wherein
in a case where two directions perpendicular to the longitudinal axis and perpendicular to the first perpendicular direction and the second perpendicular direction are defined as a third perpendicular direction and a fourth perpendicular direction, the exposed surface of the treating section includes a second curved exposed portion facing toward the proximal direction in the curved projecting portion, a third curved exposed portion facing toward the third perpendicular direction in the curved projecting portion, and a fourth curved exposed portion facing toward the fourth perpendicular direction in the curved projecting portion, and
the index portion is disposed in at least one of the first curved exposed portion, the second curved exposed portion, the third curved exposed portion, and the fourth curved exposed portion.

11. The ultrasonic probe of claim 8, wherein
the treating section is extended along the longitudinal axis without being curved,
the exposed surface of the treating section includes a first outer periphery exposed portion facing toward the first perpendicular direction in an outer periphery of the treating section, a second outer periphery exposed portion facing toward the second perpendicular direction in the outer periphery of the treating section, and a relay exposed portion extended continuously along the first perpendicular direction and the second perpendicular direction between the first outer periphery exposed portion and the second outer periphery exposed portion,
the treating section includes a hole defining surface which defines an opening hole opened at a first opening end positioned in the first outer periphery exposed portion, and which is extended from the first opening end toward the second perpendicular direction,
the contact portion is positioned at the first opening end of the opening hole, and
the index portion is disposed in the relay exposed portion.

12. The ultrasonic probe of claim 11, wherein
the opening hole opens at a second opening end positioned in the second outer periphery exposed portion, and penetrates the treating section along the first perpendicular direction and the second perpendicular direction between the first opening end and the second opening end, and the relay exposed portion includes an outer relay portion positioned in an outside of the opening hole, and an inner relay portion as the hole defining surface which defines the opening hole.

* * * * *